United States Patent [19]
Kelly

[11] Patent Number: 4,716,448
[45] Date of Patent: Dec. 29, 1987

[54] CHEMFET OPERATION WITHOUT A REFERENCE ELECTRODE

[76] Inventor: Kevin A. Kelly, 858 Kinnear Rd., Apt. #213, Columbus, Ohio 43212

[21] Appl. No.: 771,974

[22] Filed: Sep. 3, 1985

[51] Int. Cl.⁴ .............................................. H01L 29/66
[52] U.S. Cl. ..................................... 357/25; 307/308; 324/71.5; 204/406
[58] Field of Search ......................... 357/25; 324/71.5; 307/308; 204/406, 412, 416

[56] References Cited

U.S. PATENT DOCUMENTS 4,020,830  5/1977  Johnson ................................. 357/25
4,269,682  5/1981  Yano ................................... 204/418
4,488,556  12/1984  Ho ........................................ 357/25

FOREIGN PATENT DOCUMENTS 56-82440  7/1981  Japan ................................... 204/406

Primary Examiner—Andrew J. James
Assistant Examiner—Mark Prenty
Attorney, Agent, or Firm—Pearne, Gordon, McCoy & Granger

[57] ABSTRACT

A depletion mode chemically sensitive field effect transducer device has a gate region adapted to interface with a solution so as to generate an electrochemical interfacial potential. A d.c. voltage potential is applied between the source and drain to cause a source-drain current to flow when a variable conductance channel connects the source and drain. A time-variant bulk potential is applied to the substrate and alternately opens and closes the conductive channel. The chemical property of interest of the solution thus can be determined by variations in bulk threshold voltage levels at which a predetermined source-drain current flows, without the use of a reference electrode in contact with the solution.

24 Claims, 7 Drawing Figures 4,716,448

CHEMFET OPERATION WITHOUT A REFERENCE ELECTRODE

BACKGROUND OF THE INVENTION

1. Technical Field

The invention relates generally to chemically sensitive field effect transducers and like devices. More specifically, the invention relates to a mode of operating such devices without the use of a reference electrode.

2. Description of the Related Art

Chemically sensitive field effect transducers or transistors (CHEMFETs) have been the subject of extensive research and commercial applications in both industrial and medical technology fields. In medical applications in particular, measurement and monitoring of chemical properties such as the presence, activity, and concentration of chemical and biochemical substances such as ions, enzymes, antibodies, antigens, hormones, and reducible gases, are important for proper diagnosis and treatment. In a variety of in vivo and in vitro situations, there is a need for miniaturizing the measuring apparatus, as well as improving the speed and reducing the cost of performing the measurements. The utilization of CHEMFETs is desirable due to their small size and large volume production aspects resulting in reduced cost.

The term "CHEMFET" as used hereinafter designates a device which functionally operates like a conventional insulated-gate field effect transistor (IGFET or MOSFET) but in which the conducting metal gate layer is omitted or replaced with a chemically sensitive region or membrane. One such device is described in U.S. Pat. No. 4,020,830 issued to Johnson et al. and the teachings of that patent are fully incorporated herein by reference. It is common in the art to classify CHEMFETs of the type described by Johnson et al. by the nature of the chemically sensitive system and the substances with which they react. Thus, ion sensitive devices are usually designated "ISFETs" and immunological devices are commonly known as "IMFETs." The present invention is not limited to any particular class of CHEMFET and the use of this term should not be interpreted in a limiting sense. Accordingly, as used herein, "CHEMFET" refers to any device of the generally described type irrespective of the particular chemical system such device is adapted to interface with or other variations such as whether or not they use separate insulator and membrane layers, and so on. The particular structures and methodologies of making CHEMFETs is well known and not considered part of the present invention.

Generally, a CHEMFET is a field effect device functionally analogous to a conventional MOSFET. A semiconductor substrate is formed with source and drain regions separated by a variably conductive channel. In a MOSFET, a gate region overlays the channel and includes an insulator layer such as silicon dioxide and a gate metal contact layer thereon such as aluminum. A CHEMFET, on the other hand, replaces the gate metal contact and/or the gate region insulator layer with a chemically sensitive region or membrane particularly selected and adapted for the substance and chemical properties under test. The conductivity of the channel varies in relation to the interfacial potential between the sensitive region and the substance. Thus, a measurement of the interfacial potential or the channel conductivity corresponds to a measurement of the particular chemical property or activity of interest.

A significant problem with the use of CHEMFETs is the lack of reproducible measurements when monitoring the channel conductivity, as by measuring the source-to-drain current. Thus, it is common practice to use a reference electrode to bias the CHEMFET at a predetermined operating point or to use the reference electrode as a negative Feedback element. This latter technique permits measurement of the interfacial potential, and thus the chemical property of interest. For example, Johnson et al. show the use of a reference electrode with an enhancement mode device to establish a conductive channel, and the potential at the substance/gate membrane interface varies the channel conductance, and hence the measured source-to-drain current. U.S. Pat. No. 4,488,556, issued to Ho, shows a system wherein the gate region of the transducer is maintained at a potential equal to the combination of a reference electrode potential plus the electrochemical potential generated at the membrane/substance interface. With this technique, the use of the reference electrode permits a means for measuring differences in the interfacial potential caused by changes in the chemical properties under test and provides more reproducible measurements, since the interfacial potential exhibits less drift than the corresponding source/drain current.

While the CHEMFET applications known heretofore are useful for their intended purpose, the required reference electrode is an undesirable aspect of such systems. The term "reference electrode" as used herein includes standard nonpolarizable devices for maintaining constant liquid junction potentials, such as standard calomel and silver-silver chloride electrodes, as well as polarizable electrodes such as described in U.S. Pat. No. 4,269,682, issued to Yano et al. A typical reference electrode is unsuitable for in vivo implant applications because of its large size, but when the reference electrode is miniaturized, measurement values become more unstable and unreliable, and the electrode has a shorter useful life.

While some advances have been made in improving the design of the reference electrode. For example see U.S. Pat. No. 4,269,682, supra, it is clear that any application which requires use of a reference electrode to obtain reproducible results will be necessarily and undesirably limited and more costly. It is apparent that the need has long existed for a way to utilize CHEMFETs effectively without a reference electrode.

SUMMARY OF THE INVENTION

The invention provides an improved mode of operation for a CHEMFET which results in reproducible measurements without the use of a reference electrode. According to one aspect of the invention, a conventional CHEMFET is operated in the linear, non-saturated region with a predetermined d.c potential between the source and drain and with a time-variant a.c. potential applied to the substrate. The CHEMFET is preferably a depletion mode device such that the substrate potential alternately opens and closes a conductive channel between the source and drain. The channel is considered to be open when a predetermined current flows between the source and drain.

According to another aspect of the invention, a CHEMFET device is operated with a chemically sensitive gate region in fluid contact with a solution having one or more chemical properties under test. The gate region provides a membrane or other chemically sensitive means which develops a potential at the interface of the device and the solution. This interfacial potential varies the conductance of the channel and the substrate threshold voltage at which the channel opens. A useful relationship exists between the threshold voltage and the interfacial potential which results from the chemical activity, and thus measurement of the chemical properties is facilitated.

According to a further aspect of the invention, a circuit is provided which, in combination with a conventional CHEMFET, provides a mode of operation which achieves stable and reproducible measurements of chemical properties of a solution under test without the use of a reference electrode.

These and other aspects of the present invention will be more fully explained and understood from the following specification in view of the accompanying drawings.

DESCRIPTION OF THE PREFERRED EMBODIMENT

Figure 1:
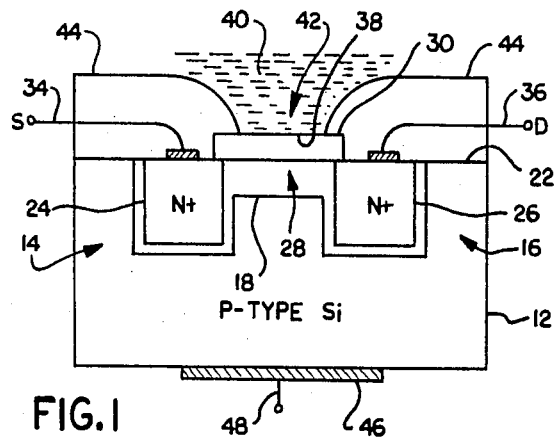
FIG. 1 is a cross-sectional view of a conventional CHEMFET suitable for use with the present invention.

A conventional depletion mode CHEMFET transducer device suitable for use with the invention is generally indicated by the numeral 10 in FIG. 1. Such a device 10 includes an electrical portion having a substrate 12, a source 14, a drain 16, and a variably conductive channel 18 underlying a chemically sensitive region. The device shown in FIG. 1 is commonly referred to as a "depletion mode" device because of the presence of a conductive channel between the source and drain in the absence of a gate bias potential.

While the preferred embodiment of the invention is described hereinafter with particularity as utilizing an "n channel" depletion mode CHEMFET device, such description is exemplary only and should not be interpreted in a limited sense. Thus, the present invention contemplates other chemical/electrical transducer devices, such as p channel CHEMFETs and n or p-channel CHEMFETs of the depletion/enhancement mode type. Furthermore, while the described transducer is a CHEMFET particularly adapted for measuring and sensing pH levels of a solution based on the ionic activity of the solution with a chemically sensitive gate region, the invention is not limited to such use and can be utilized with many types of CHEMFETs which are sensitive to various chemical properties, activities, and concentrations of chemical substances, such as ions, enzymes, antibodies, antigens, hormones, and reducible gases. The particular CHEMFET selected will depend on the particular substance under test and the particular chemical properties being measured or sensed. Thus, the term CHEMFET should be interpreted broadly as any one in that class of devices of the generally described type. The particular techniques and methodologies for manufacturing the CHEMFETs are well known in the art and not considered part of the present invention, the invention being directed to a new operating mode for such devices.

Returning to FIG. 1, the substrate 12 is made of a suitable semiconductor material, typically silicon, and has a p-type doping polarity. One surface 22 of the substrate has two spaced-apart diffusion regions 24 and 26 having an n+ type highly doped polarity. These regions 24, 26 are conventionally designated the source and drain, respectively. Subsequent and between the source 24 and drain 26 is the channel region 18. The channel 18 is formed by free conducting electrons resulting from trapped positive charges at the lattice interface of the silicon substrate 12 and an oxide layer 30 which will be described shortly. Alternatively, the channel 18 can be formed by other well known methods. For example, an n-type material may be ion-implanted.

The area 28 of the substrate 12 between the source 24 and drain 26 is commonly referred to as the gate or gate region. The illustrated device 10 is referred to as a depletion mode device because the conductive channel 18 is present between the source and drain when no electrical potential is applied to the gate region.

An electrical insulator layer 30, typically silicon dioxide or a silicon dioxide/silicon nitride sandwich, is thermally grown on the surface of the substrate 12, particularly over the gate region 28 and portions of the diffused regions 24, 26. A suitable conductive metal layer 32, such as aluminum, is deposited on the source and drain region surfaces to provide ohmic contact areas For a source lead wire 34 and a drain lead wire 36.

The structure of the CHEMFET 10 as described thus far can be adapted to measure different chemical properties, concentrations, or activities of a substance, for example, ions, enzymes, reducible gases, etc., by providing an appropriate chemically selective region which overlays or replaces the insulative layer 30 above the gate region 28. Such a chemically selective system is adapted to interact with certain substances to which it is exposed, thereby producing an electrochemical potential at the interface of the substance and the chemically sensitive layer. This interfacial potential modulates the electrical conductance of the channel 18 between the diffused regions 24, 26.

For measuring or sensing ion activity such as would be desirable for detecting pH levels of a substance or electrolytic solution 40. FIG. 1 illustrates the simplest chemically selective region in that the gate oxide layer 30 can also act as a suitable chemically sensitive agent. Thus, the exposed oxide surface 38, when placed in contact with the substance 40 under test, reacts therewith, creating an electrochemical potential corresponding to the pH of the substance at the interface area 42 between the insulator 30 and the substance 40. Of course, silicon dioxide used as the layer 30 can be replaced with a more suitable insulative material if hydration is likely to occur, or a chemically sensitive membrane can be deposited on or used in place of the insulator layer 30 for specific situations wherein other chemical properties are to be determined.

Since the device 10, when adapted for detection of pH, would typically be immersed in or exposed to the solution 40 in question, it is desirable that all except a portion of the interface area 42 be covered with some type of solution-impervious material. A passivation layer 44 represents such material and might, for example, comprise a polymerized epoxy resin. It should be understood that the solution-impervious material would cover all parts of the device, including electrical leads, etc., which might be immersed in the solution. The type of solution-imperivous material used, of course, would depend upon the kinds of solution into which the transducer was to be immersed, but generally the material should be at least water-impervious, and preferably biocompatible, i.e., should not adversely interact with the solution or tissue to which the device is exposed.

An electrically conductive layer 46, such as aluminum, is deposited on the back side of the substrate 12 opposite the gate region, and provides an ohmic contact area for a substrate lead 48.

Figure 2:
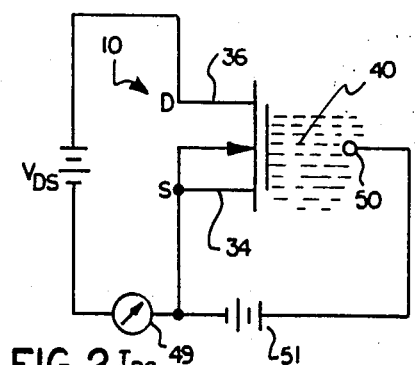
FIG. 2 is a schematic representation of a biasing scheme for operating the CHEMFET shown in FIG. 1, as known in the prior art.

The conventional operation of the device 10 will now be described. Referring to FIGS. 1 and 2, a relatively small constant d.c. voltage potential $V_{DS}$ (for example, 0.5 volts) is applied between the source 24 and the drain 26. Because the CHEMFET 10 is a depletion mode device, the conductive channel 18 is present between and connects the source and drain even when no bias potential is applied at the gate 28. The potential $V_{DS}$ thus causes a source-to-drain current, $I_{DS}$, to flow which can be measured with a current meter 49. The potential $V_{DS}$ is maintained at a relatively low value so that the device 10 operates in the linear (non-saturated) region with respect to $I_{DS}$ and $V_{DS}$. Operating the device in the linear region generally increases the sensitivity of the device 10.

The effect of the interfacial potential at location 42 between the test substance 40 and the chemically sensitive system (the oxide 30 as illustrated) is as follows. When the two phases 40,30 of different chemical composition come into intimate contact, there is generally a charge separation, and thus an electrical energy potential, between the two phases at the interface 42 thereof. In the case of an oxide insulator and an electrolytic substance 40 interface, the potential can arise from surface state and site-binding mechanisms, to name two. In any case, the interfacial potential is ideally determined only by the activity, concentration or presence of the specific ion or other chemical property of interest as selectively determined by the preselected chemically sensitive system as described previously.

The resultant interfacial potential is an effective gate voltage ($V_G$) in that it is able to modulate the conductance of the channel 18 between the source 24 and the drain 26. By way of example, for a pH measurement, the relative pH of the substance 40 determines (via ion activity with the oxide layer 30 at the interface 42) an interfacial potential which in turn determines the conductance of the channel 18. Thus, measurement of the chemical property of interest, or changes thereof such as pH, can be accomplished by measurement or sensing of the corresponding variations or changes of the effective interfacial potential or the resultant conductance of the channel 18.

Measurement of the corresponding conductance of the channel 18, of course, can be accomplished by simply measuring the current $I_{DS}$, as in FIG. 2. However, as a practical matter, a reference electrode 50 (FIG. 2) is required in the prior art to achieve repeatable and reliable results. The reference electrode is used with a supply 51 to establish a reference potential in the solution or substance 40, and thus, particularly in the case of an enhancement mode device, establish a suitable operating point for the device 10. Variations or drift in the channel conductance due to effects other than changes in the interfacial potential seem to be effectively reduced by use of the reference electrode.

Figure 3:
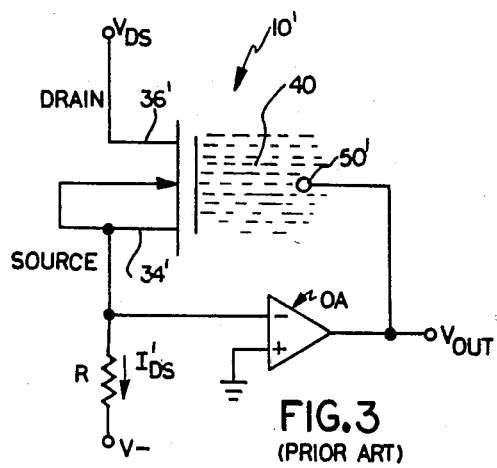
FIG. 3 is a schematic diagram of another circuit for operating the CHEMFET shown in FIG. 1 according to the prior art.

FIG. 3 shows another circuit known heretofore to measure or sense chemical properties with a CHEMFET. This circuit utilizes the chemically selective system and solution interface 42 as a half-cell potential generator. The half-cell circuit is completed by use of a reference electrode 50'. Thus, the potential of the composite cell varies with changes in the chemical activity of interest such as pH, i.e., the CHEMFET 10' is operated with a constant current source defined by the resistor R and the voltage supply V. The op-amp, OA, is operated in a negative feedback mode so that the source 34' of the CHEMFET is maintained at a virtual ground. The sum of the reference electrode potential and the CHEMFET interfacial potential must be a constant in order for the constant current $I'_{DS}$ to flow. Thus, corresponding variations of the interfacial potential with the chemical property being sensed, such as pH, show up as equivalent variations in the reference electrode potential only in the opposite direction. The circuit of FIG. 3 thus actually detects or measures the interfacial potential rather than strictly relying on measurement of changes in $I'_{DS}$ (which correspond to channel conductance variations), so that repeatability is somewhat improved.

As described, however, the use of a reference electrode is undesirable, particularly in applications requiring in vivo implants.

Figure 4:
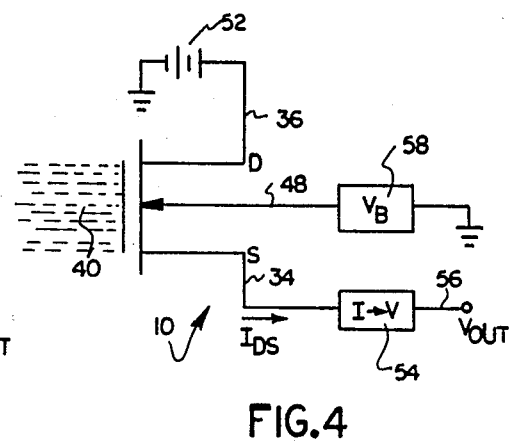
FIG. 4 is a schematic diagram of a circuit in accordance with the teachings and concepts of the invention.

The present invention provides an improved method and means for operating a conventional CHEMFET to obtain repeatable results without the use of a reference electrode. Turning to FIG. 4, a circuit is shown which is suitable for use with the present invention. Features which correspond to those in FIGS. 1 and 2 are given like numerals.

The invention generally contemplates obviating the need for a reference electrode by the use of bulk voltage modulation. As illustrated, an n-channel depletion mode CHEMFET 10 has the chemically selective system exposed to a solution/substance 40 under test. A small voltage potential of about +0.5 volts is applied to the drain lead 36 via a power supply 52. The source lead 34 is connected to the input of a current-to-voltage converter 54 which provides an output signal on the signal line 56. The input characteristics of the converter 54 are such that the source 24 is held at a virtual ground. Thus, the drain and source are biased such that a current $I_{DS}$ flows between the source and drain. The converter 54 detects the current $I_{DS}$ and converts it to a corresponding voltage signal which can be easily detected at the output 56 thereof. Specific circuitry for implementing the converter 54, as with a common differential amplifier, is well known in the art.

A time variant bulk voltage, $V_B$, is applied to the substrate lead 48 via a supply 58. The particular time-variant potential waveform selected may be triangular, square, sinusoidal, or any other suitable form depending on the particular CHEMFET used and chemical property to be tested. Particular supply circuits 58 for producing such signal waveforms are well known to those skilled in the art, and do not constitute part of the invention. The potential applied to the substrate 12, however, must be less than the forward bias voltage of the source/substrate junction. By way of example, the substrate can be ramped between plus and minus 300 millivolts, although other ranges may be selected depending on the actual channel threshold voltage of the device 10 in use.

In operation, the application of a time-variant potential to the substrate 12 via the contact 46 and lead 48 causes the conductive channel 18 to alternately open and close when the substrate voltage is respectively greater than or less than the channel threshold voltage. The channel threshold voltage is that voltage at which the conductive channel 18 between the source and drain is present. With an n-channel device, when the substrate (i.e., bulk) potential is sufficiently negative, the channel 18 is prevented by being depleted of carriers so that no current flows between source and drain and the channel is commonly referred to as being closed. As the substrate voltage is increased in a positive direction, the channel is promoted and commonly referred to as open and a substantial current $I_{DS}$ flows. Typically, the frequency of the time-variant potential will be relatively low, e.g., less than one cycle per six seconds; however, moderately higher frequencies can be used depending on the response speed of the particular device being used.

The actual value of the threshold voltage or potential, of course, will depend on the manufacturer's processing particulars of the device 10 used. For purposes of having a predetermined standard, a current value $I_{DS}$ can be arbitrarily selected for which the channel is considered to be open. The substrate potential, then, at which this predetermined $I_{DS}$ current level flows is defined herein to be the channel or bulk threshold voltage $V_T$.

Once the channel threshold voltage $V_T$ has been defined with respect to $I_{DS}$, the bulk modulation operating method provides a reliable system for measuring the chemical property of interest of the substance 40. This follows from the discovery that the interfacial potential between the substance 40 and the chemically selective system changes the channel threshold voltage in a useful manner.

Figure 5:
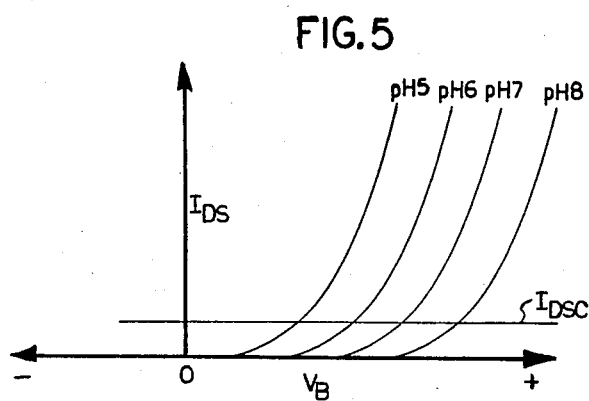
FIG. 5 is a graph depicting a family of curves which show typical relationship between a time-variant substrate voltage and the drain/source current at different pH levels.

Using the pH of a solution as an example, FIG. 5 ideally shows a typical graph of the relationship between the source-drain current $I_{DS}$ and a variant substrate voltage $V_B$. In this particular example, the threshold voltage at which the channel 18 is present is about 0 volts d.c. Thus, $V_B$ is ramped between ±300 millivolts. Looking for the moment only at the leftmost curve (designated pH 5), it can be seen that as the bulk voltage $V_B$ becomes more positive, the drain-source current increases dramatically. The current-voltage relation ship, of course, is non-linear for typical deplation mode devices.

The remaining curves included on FIG. 5 show the current voltage relationship at different pH levels of the solution 40. While the general non-linear shapes of the curves are similar (they all asymptotically approach $I_{DS}=0$ as $V_B$ tends to go negative), it will be noted that at higher pH values, the curves are somewhat transposed further out along the X axis. The significance of this characteristic is that the relative pH of the solution changes the bulk voltage required to permit a given current level to flow. This is because the interfacial potential between the solution 40 and the oxide 30 changes the threshold voltage at which the channel is open.

By way of example, a constant current line $I_{DSC}$ has been drawn superimposed on FIG. 5 at about 0.25 microamperes. This constant current $I_{DSC}$ can be somewhat arbitrarily selected to achieve the most consistent results based on the particular CHEMFET being used. This current then is designated as the drain-source current flow for which the channel 18 is considered to be open. The channel threshold voltage $V_T$ can be thought of as that value of the bulk voltage at which the current $I_{DSC}$ flows. As shown in FIG. 5, this channel threshold voltage $V_T$ is a function of the pH level of the solution 40.

Figure 5A:
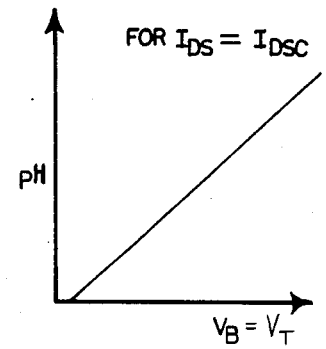
FIG. 5A is another graph of the data depicted in FIG. 5.

FIG. 5A shows another graph of the data depicted in FIG. 5, and in particular shows the relationship between the channel threshold voltage $V_T$ and the pH of the solution at a predetermined current $I_{DSC}$. Of particular interest in the fact that the two parameters are defined by a repeatable linear relationship. Thus, for a predetermined constant current $I_{DSC}$, a measurement of the bulk voltage $V_B$ at which such current $I_{DSC}$ flows (i.e., $V_T$) is directly indicative of the pH of the solution 40. It should now be clear that the value of $I_{DSC}$ can be conveniently selected for characterizing a device 10 to provide the most linear relationship between the pH and $V_T$ for any particular device 10 being used at the time of measurement.

The described mode of operating the CHEMFET 10 with bulk voltage modulation results in repeatable measurements in that after a few substrate bulk voltage cycles (about 15), the CHEMFETs reach an equilibrium or dynamic steady state. That is, the $I_{DS}$ vs. $V_B$ curves (such as shown in FIG. 5) exhibit minimal drift when the bulk voltage $V_B$ is alternately varied between two fixed extremes (e.g., ±300 mv.) at a consistent rate. A particularly suitable rate has been found to be 50 millivolts/second when using a triangular waveform. As stated, however, other time variant waveform and ramp rates can be selected to obtain optimal results. By making measurements after the device 10 has reached its dynamic steady state, the pH of the solution 40 can be sensed with reliable and reproducible results without the need for a reference electrode in the solution.

Figure 6:
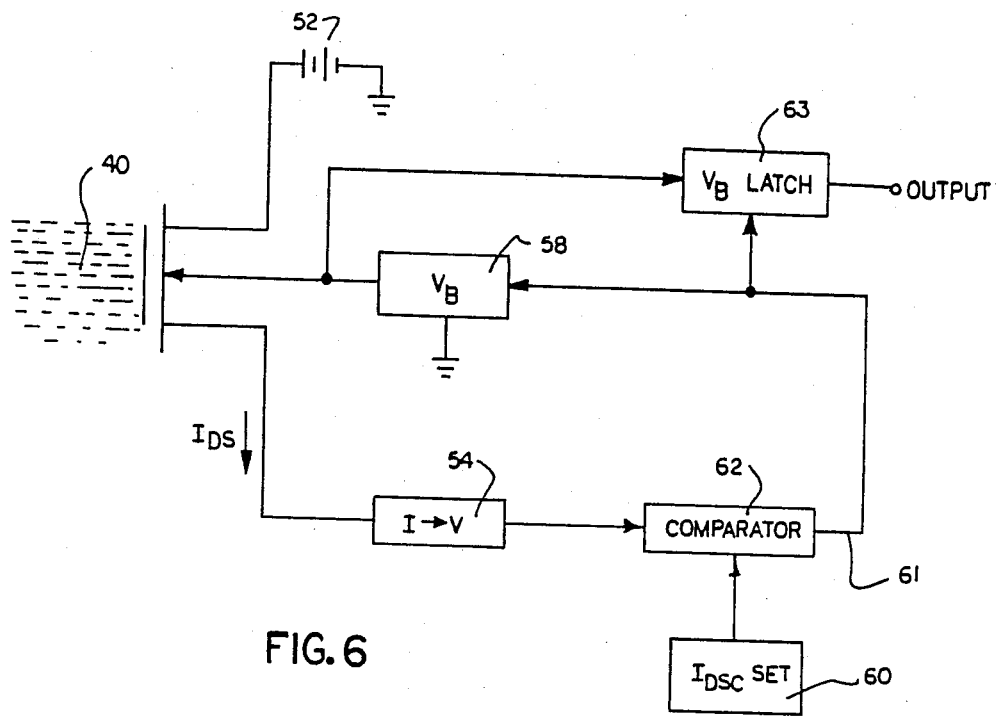
FIG. 6 is another embodiment of a circuit in accordance with the invention.

The circuit shown in FIG. 4 is a test circuit which can be used to generate the family of curves shown in FIG. 5. It is contemplated that in clinical or industrial use a circuit can be easily designed which will automatically perform the measurements of the chemical properties of interest and such circuits can be controlled by microprocessors or other known controllers. One such circuit is shown in FIG. 6. The substrate 12 via the substrate lead 48 has a time-variant potential from supply 58 applied thereto as described and a power supply 52 provides a low d.c. bias between the source and drain. The drain-source current $I_{DS}$ is sensed by a current-to-voltage converter 54 the output of which is fed to one input of a comparator 62. A predetermined current set point circuit 60 generates a voltage which corresponds to the predeterminable level of $I_{DSC}$ (which designates that the channel 18 is open) after the particular device 10 has been characterized. The output of circuit 60 is fed to the other input of the comparator 62. The comparator 62 detects the occurrence and provides an output 61 indication when the drain-source current $I_{DS}$ substantially equals the predetermined current level $I_{DSC}$ as selected by the adjustable circuit 60 (which occurs when $V_B=V_T$, as defined hereinabove). The output 61 of the comparator 62 can be used as a control signal which is fed back to the time-variant source 58 and reverses the direction of the ramping bulk voltage potential. Thus, the bulk voltage $V_B$ is only increased to that value ($V_T$) when the channel 18 is considered to be open (i.e., $I_{DS}=I_{DSC}$). For example, if the circuit of FIG. 6 were used with the device having operating characteristics like those represented in FIG. 5, the family of curves would only extend up to the constant current line $I_{DS}=0.25$ A. This feature of reversing the ramp direction of $V_B$ as soon as the $V_B=V_T$ condition is met thus substantially reduces the test time required. The output of the comparator 62 can also be used to trigger a bulk voltage latch 63 used to store the value of $V_B=V_T$, at which the predetermined source-drain current $I_{DSC}$ flows.

While the invention has been shown and described with respect to a particular embodiment thereof, this is for the purpose of illustration rather than limitation, and other variations and modifications of the specific embodiment herein shown and described will be apparent to those skilled in the art all within the intended spirit and scope of the invention. Accordingly, the patent is not to be limited in scope and effect to the specific embodiment herein shown and described nor in any other way that is inconsistent with the extent to which the progress in the art has been advanced by the invention.

What is claimed is:

1. In combination, a chemically sensitive field effect transducer having a gate region adapted to interface with a substance so as to generate an electrochemical interfacial potential in response to a chemical property of the substance and further having source, drain, and substrate regions, at least a portion of said substrate region being between the source and the drain, first means for applying a potential between the source and drain, and second means for applying a time-variant potential to the substrate.

2. The combination of claim 1, wherein said substrate potential means permits reproducible measurement of said chemical property without the use of a referene electrode contacting the substance.

3. The combination of claim 1, wherein said substrate potential means alternately opens and closes a conductive channel connecting the source and drain.

4. The combination of claim 3, wherein said channel has a conductance which varies in response to said electrochemical potential.

5. The combination of claim 4, wherein said source-drain potential means causes a current flow between the source and drain in response to said substrate potential.

6. The combination of claim 5, wherein said substrate potential is a time-variant voltage which alternately changes between two predetermined values, there being a channel threshold voltage between said predetermined values at which said channel is designated as being open.

7. The combination of claim 6, wherein said channel threshold voltage is that voltage at which a predetermined current flows between the source and drain.

8. The combination of claim 7, wherein said channel threshold voltage varies in response to said electrochemical potential such that chemical properties of the substance can be determined by measurement of said channel threshold voltage after the transducer has reached a dynamic steady state.

9. The combination of claim 8, wherein the chemically sensitive field effect transducer is a depletion mode or a depletion enhancement mode device.

10. The combination of claim 8, wherein said transducer is adapted to detect pH levels of a solution.

11. The combination of claim 8, further comprising means for converting said source-drain current to a corresponding signal and means for comparing said corresponding signal with a predetermined current limit signal, said comparator means producing a control signal indicative of said source-drain current substantially equaling said predetermined limit.

12. The combination of claim 11, further comprising latch means for storing a value of said substrate potential in response to said control signal.

13. The combination of claim 12, wherein said stored substrate potential corresponds to said channel threshold voltage.

14. The combination of claim 11, wherein said substrate potential means provides a low frequency signal which normally ramps between said two predetermined values but which is reversed in response to said control signal.

15. An apparatus for detecting chemical properties of a solution without the use of a reference electrode, comprising a chemically sensitive FET having a gate region adapted to interface with the solution to produce an interfacial potential corresponding to a chemical property of the solution and further having source, drain, and substrate regions, first means for causing a current to flow between the source and drain when a conductive channel is present, and second means for applying a time-variant bulk voltage to the substrate so as to alternately promote and prevent a conductive channel connecting the source and drain, there being a bulk threshold voltage at which a predetermined current flows between the source and the drain, said threshold voltage varying in response to changes of said interfacial potential.

16. An apparatus according to claim 15, wherein said FET is a depletion mode or a depletion-enhancement mode device.

17. An apparatus according to claim 15, wherein said time-variant bulk voltage means provides a substrate voltage which alternately varies between two predetermined values in a cyclical manner, said substrate voltage ramping through said bulk threshold voltage so as to alternately open and close said conductive channel.

18. An apparatus according to claim 15, wherein said interfacial potential modulates said channel conductance and thus said bulk threshold voltage, thereby permitting a determination of different chemical properties of the solution by measuring variations in said bulk threshold voltage at a predetermined source-drain current level after the FET has reached a dynamic steady state.

19. An apparatus according to claim 18, wherein said predetermined current level defines a linear relationship between variations in said bulk threshold voltage and changes in chemical properties of the solution.

20. An apparatus according to claim 15, further comprising means for determining said bulk threshold voltage when a predetermined source-drain current is present.

21. An apparatus according to claim 20, further comprising means for changing said time-variant substrate voltage when said predetermined source-drain current is present.

22. An apparatus according to claim 15, wherein said time-variant bulk voltage is a low frequency signal.

23. An apparatus according to claim 22, wherein said time-variant bulk voltage has a signal frequency of less than one cycle per second.

24. An apparatus according to claim 17, wherein said substrate voltage ramps through said bulk voltage threshold at an approximate rate of 50 mvolts/sec.

* * * * *

UNITED STATES PATENT AND TRADEMARK OFFICE
CERTIFICATE OF CORRECTION

PATENT NO. : 4,716,448
DATED : December 29, 1987
INVENTOR(S) : Kevin A. Kelly

It is certified that error appears in the above-identified patent and that said Letters Patent is hereby corrected as shown below:

Column 10, line 3, change "depletion enhancement" to --depletion-enhancement--.

Column 2, line 9, change "Feedback" to --feedback--;
  line 43, change "." to --,--; and
  line 43, change "For" to --for--.

Column 3, line 33, change "relationship" to --relationships--;
  line 55, change "n channel" to --n-channel--; and
  line 59, change "p channel" to --p-channel--.

Column 4, line 40, change "For" to --for--; and
  line 57, change "." to --,--.

Column 7, line 57, change "relation ship" to --relationship--; and
  lines 57 and 58, change "deplation" to --depletion--.

Column 8, line 20, change "in" to --is--; and
  line 40, change "time variant waveform" to --time-variant waveforms--.

Signed and Sealed this

Twenty-sixth Day of July, 1988

Attest:

DONALD J. QUIGG

Attesting Officer

Commissioner of Patents and Trademarks